United States Patent [19]

Adair

[11] Patent Number: 4,869,246

[45] Date of Patent: Sep. 26, 1989

[54] METHOD FOR CONTROLLABLY EMBOLYZING BLOOD VESSELS

[76] Inventor: Edwin L. Adair, 2800 S. University Blvd., Denver, Colo. 80210

[21] Appl. No.: 131,673

[22] Filed: Dec. 11, 1987

[51] Int. Cl.$^4$ .............................................. A61M 1/30
[52] U.S. Cl. ................................. 128/303.1; 128/398; 604/22
[58] Field of Search ...................... 129/362, 303.1, 395, 129/397, 398, 4–6; 604/95–99, 22–26

[56] References Cited

U.S. PATENT DOCUMENTS

| | | | |
|---|---|---|---|
| 3,833,003 | 9/1924 | Taricco | 604/46 |
| 3,870,072 | 3/1975 | Lindemann . | |
| 4,248,222 | 2/1981 | Jaeger et al. | 604/98 |
| 4,258,721 | 3/1981 | Parent et al. . | |
| 4,345,602 | 8/1982 | Yoshimura et al. | 604/23 |
| 4,445,892 | 5/1984 | Hussein et al. | 128/4 |
| 4,446,867 | 5/1984 | Leveen et al. | 604/97 |
| 4,448,188 | 5/1984 | Loeb | 604/96 |
| 4,508,177 | 4/1985 | Rodari | 128/205.24 |
| 4,512,762 | 4/1985 | Spears | 128/303.1 |
| 4,559,942 | 12/1985 | Eisenberg | 128/395 |
| 4,648,386 | 3/1987 | Morritt et al. . | |
| 4,737,142 | 4/1988 | Heckele | 604/95 |
| 4,753,223 | 6/1988 | Bremer | 604/95 |
| 4,770,653 | 9/1988 | Shturman | 604/96 |

Primary Examiner—Lee S. Cohen
Assistant Examiner—David Shay
Attorney, Agent, or Firm—Fields, Lewis, Pittenger & Rost

[57] ABSTRACT

A method and system for controllably gas embolyzing a portion of a blood vessel is disclosed. The method includes providing an obstruction to the flow of blood in a blood vessel and introducing sufficient gas, preferably carbon dioxide, into the blood vessel at a location adjacent the obstruction to create a controlled segmental embolism in the blood vessel adjacent the obstruction. The carbon dioxide fed embolism clears blood away from a portion of the blood vessel to provide a blood-free area which can be easily viewed by a physician looking through an endoscope. The method is carried out with a catheterization system which includes means for providing a controlled obstruction to the flow of blood in a blood vessel and tubular means defining a channel for conducting sufficient gas into the blood vessel at a location adjacent the controlled obstruction to create a controlled gas embolism in the vessel adjacent the obstruction.

10 Claims, 1 Drawing Sheet

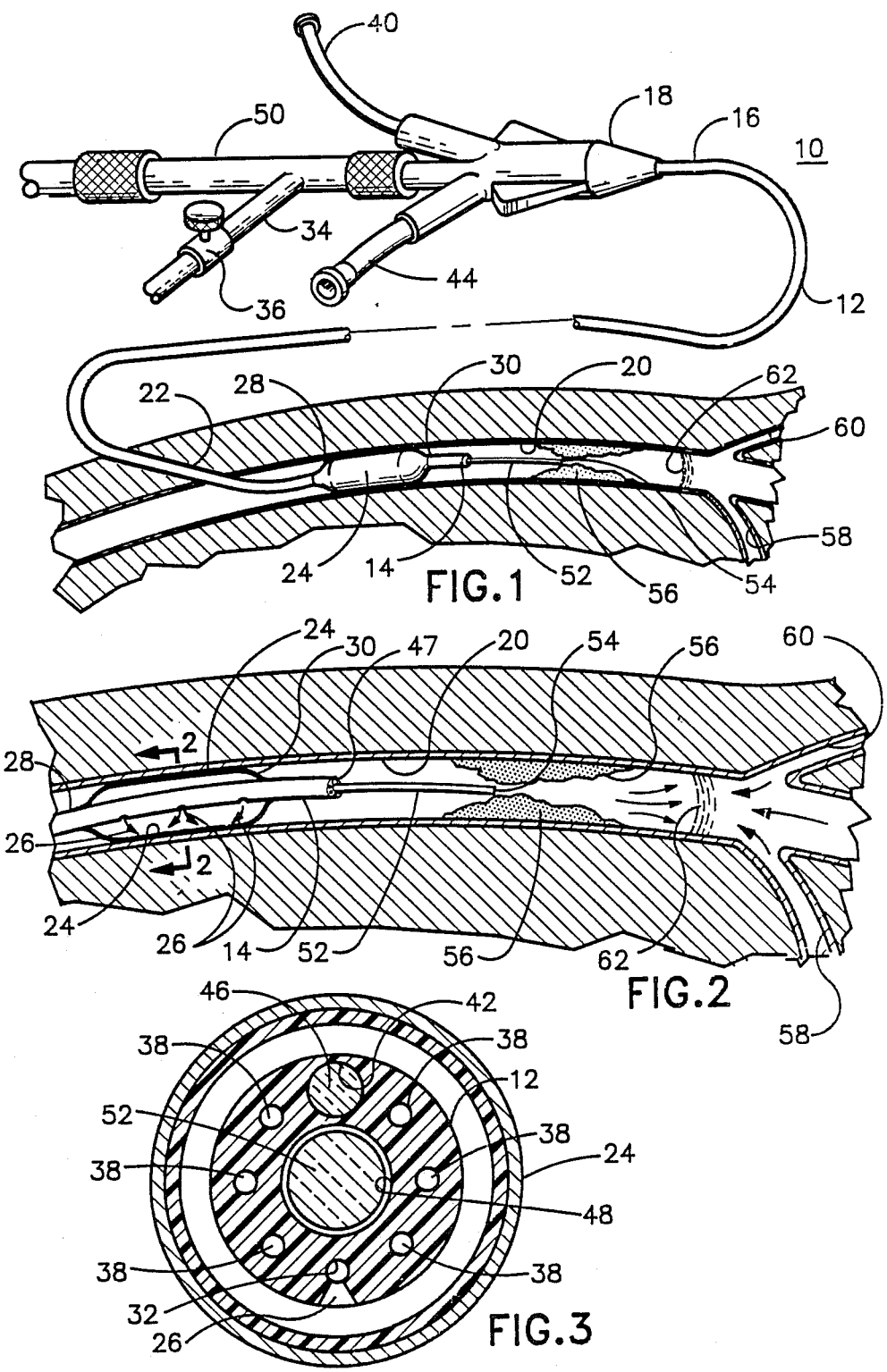

METHOD FOR CONTROLLABLY EMBOLYZING BLOOD VESSELS

TECHNICAL FIELD

The invention relates generally to a method and system for facilitating intra-arterial procedures, and more particularly, to a method and system which will enable a physician to directly view the interior of a blood vessel and perform intra-arterial procedures under such direct vision.

BACKGROUND ART

If it were possible to remove blood from portions of blood vessels, certain intra-arterial procedures could be performed under direct vision which would greatly enhance the procedures' effectiveness and success rate. For instance, it would make intra-arterial laser removal of obstructing plaque much easier and safer. It would also greatly improve the efficacy and safety of treating arteriosclerosis by phototheraphy.

U.S. Pat. No. 3,870,072 to Lindemann and U.S. Pat. No. 4,258,721 to Parent, et al. both disclose the concept of injecting carbon dioxide into a human body. Lindemann discusses carbon dioxide being absorbed by the blood. However, neither patent teaches the concept of injecting carbon dioxide into a blood vessel for clearing the blood to conduct a medical procedure. U.S. Pat. No. 4,648,386 teaches the use of a laser with pressurized gas but does not suggest the present invention.

Many intra-arterial procedures are now done under fluoroscopic control. Catheters impregnated with radio opaque materials are introduced into arteries and visualized as to their position by observing the radio opaque "tags". Another procedure called balloon catheter angioplasty of arteries is conducted by outlining a ballooned segment of a catheter with radio-opaque markers. The balloon is positioned in the area of a blood vessel obstruction, and the catheter balloon is inflated to stretch open the obstruction. This procedure has not been totally successful in that the obstruction sometimes immediately re-occurs due to swelling resulting from the trauma of stretching the vessel. The obstruction may also re-occur in the immediate post-operative period, requiring immediate open operative intervention, such as a bypass surgical procedure, which is one of the procedures balloon angioplasty was designed to obviate in the first place.

It has also known that lasers of various types can be used to irradiate and remove plaque, blood clots and other obstructions such as scar tissue in blood vessels. Lasers are best utilized when they can be controlled as to their direction and depth of coagulation or vaporization, which preferably requires that they be used under direct vision. Unfortunately, at the present time, there is no way of visually observing intra-arterial use of lasers except with a procedure where the blood is replaced with a clear fluid such as a normal saline solution. This procedure involves injecting a bolus of the clear fluid at the tip of the laser fiber immediately prior to irradiating the obstruction with laser energy. The bolus provides a clear field of view for short period of time which enables a physician to view the obstruction prior to irradiating it with the laser. Unfortunately, the clear field is quickly obscured by the flow of blood through the vessel, and there is rarely enough time to re-position the laser fiber if such is necessary.

Attempts to create and maintain a blood-free segment in a blood vessel have been made with a balloon which is inserted into a blood vessel and then inflated to create an obstruction to blood flow. It was thought that a blood-free segment on the downstream of the balloon obstruction would materialize when the balloon was inflated to obstruct blood flow. However, blood from small downstream tributary arteries (i.e., on the downstream side of the balloon obstruction) quickly backfilled into the area adjacent the balloon, thereby preventing the formation of the blood-free segment.

DISCLOSURE OF THE INVENTION

The present invention solves the problems of the prior art, particularly the problem of blood back-filling or back-flowing by providing a method and system for controllably gas embolyzing a blood vessel.

The method includes providing a controlled obstruction to blood flow in a blood vessel and introducing sufficient gas, preferably carbon dioxide, into the blood vessel at a location adjacent the obstruction to create a controlled gas embolism in the vessel adjacent the obstruction. The gas is preferably introduced into the blood vessel on the downstream side of the controlled obstruction to prevent downstream blood from back-filling into the area adjacent the controlled obstruction. Accordingly, a blood-free area downstream of the obstruction is established, which can be directly viewed by a physician to determine whether the area requires any medical treatment.

A catheterization system for carrying out the aforementioned method includes means for controllably providing an obstruction to the flow of blood in a blood vessel and tubular means defining a channel for conducting sufficient gas into the blood vessel at a location adjacent the controlled obstruction to create the controlled segmental embolism in the vessel adjacent the obstruction.

In a preferred embodiment, the catheterization system includes a flexible tube having a distal end for insertion into a blood vessel. The tube defines a channel for conducting sufficient embolyzing gas, preferably carbon dioxide, into the blood vessel to create a controlled segmental embolism in the blood vessel adjacent a controlled obstruction to blood flow through the blood vessel. The tube also defines a conduit for conducting pressurized fluid into an inflatable, generally cylindrical sleeve having opposite ends which fits over the tube at a location adjacent the tube's distal end. The sleeve is sealed to the outer surface of the tube at its opposite end so that pressurized gas or fluid conducted through the conduit is capable of inflating the sleeve so it expands up against the wall of a blood vessel to create the controlled obstruction to blood flow through the vessel. The catheterization system also preferably includes an endoscope slidably received in another channel defined by the tube which extends through the tube's distal end. The endoscope enables the blood-free area to be viewed so that one can determine whether any blood vessel obstructions such as plaque are present and whether medical treatment should be conducted to remove the obstructions.

The catheterization system also preferably includes a laser fiber which is slidably received in yet another channel defined by the tube which extends through the tube's distal end. The laser fiber is preferably provided with a length which enables it to be extended outwardly beyond the tube's distal end so that the fiber's distal end can be positioned near a blood vessel obstruction. A physician can then irradiate and remove the obstruction with laser energy transmitted through the fiber.

BRIEF DESCRIPTION OF THE DRAWINGS

FIG. 1 is a prospective view of a catheterization system of the present invention showing the distal end of the catheter tube inserted in a blood vessel;

FIG. 2 is an enlarged partial view taken from FIG. 1 showing the catheter's inflated sleeve in longitudinal section; and FIG. 3 is a cross sectional view taken along the lines 3—3 of FIG. 2.

BEST MODE FOR CARRYING OUT THE INVENTION

FIG. 1 illustrates a preferred embodiment of a catheter system 10 of the present invention. The system includes a flexible tube 12 preferably made from a material such as polyethylene. The tube has a distal end 14 and a proximal end 16. Proximal end 16 is connected to a connector 18 which connects tube 12 to four supply conduits to be described in detail below.

As illustrated in FIG. 1, distal end 14 of the catheter is inserted in a blood vessel 20 of a patient through a trochar (not shown) which forms a passageway 22. This point of body entry would vary, of course, depending on the blood vessel which is to be observed and treated. If the femoral artery or main artery of the leg is to be treated, entry into the body would be through the groin area in most cases.

Returning to FIG. 1, it can be seen that catheter system 10 also includes a balloon-shaped sleeve 24 which is fitted over tube 12 at a location adjacent the tube's distal end 14.

FIG. 2 shows a longitudinal sectional view of sleeve 24 wherein it can be seen that sleeve 24 is positioned on the tube so as to cover ports 26 the side of the tube. The arrows pointing out of ports 26 represent pressurized fluid such as pressurized water or carbon dioxide which is supplied to the sleeve through tube 12 and ports 26 to inflate the sleeve so that it expands up against the wall of blood vessel 20 to stop the flow of blood through the vessel. To be inflatable, sleeve 24 should be made from a resilient expandable material such as polyethylene and its ends 28 and 30 positioned on opposite sides of ports 26 must be sealed to the outer surface of tube 12 A good seal can be provided by solvent welding ends 28 and 30 to tube 12. Adhesives may also be used as well as other sealing means known to those skilled in the relevant art, all of which are considered to be within the spirit of the present invention.

Turning now to FIG. 3, it can be seen that tube 12 defines a plurality of channels. Conduit 32 is the channel through which pressurized fluid is conducted to inflate sleeve 24. Conduit 32 is in fluid communication with ports 26 and extends therefrom (or upstream) to a supply conduit branch 34 of connector 18 which is in fluid communication with a source of pressurized fluid (not shown). Conduit branch 34 is also provided with a control valve 36 which can be regulated to control the flow of pressurized fluid into inflatable sleeve 24.

Tube 12 also defines a group of peripherally spaced channels 38 which are used to conduct embolyzing gas, preferably carbon dioxide, into blood vessel 20. Each channel 38 extends through the entire tube, (i.e., from the tube's proximal end to and through the tube's distal end). At the tube's proximal end, each channel is connected to and in fluid communication with a $CO_2$ supply conduit branch 40 of connector 18 which is in fluid communication with a source of carbon dioxide (not shown). The $CO_2$ source preferably includes an intervascular insufflator (not shown) which is capable of providing precise control over the flow rate and pressure at which carbon dioxide is introduced into a blood vessel. A gas insufflator providing precise flow control, i.e., within 0.5%, available through Medical Dynamics, Inc. of Englewood, Co.

Returning to FIG. 3, it can be seen that tube 12 is provided with yet another channel, an endoscope channel 42, which also extends through the tube from the tube's proximal end 16 to and through the tube's distal end 14. Channel 42 is connected to a conduit branch 44 at the tube's proximal end. The conduit branch and channel are sized to slidably receive a catheter 46 having a distal end 47 of an endoscope (not shown). The catheter is inserted into channel 42 until its distal end 47 is flush with the tube's distal end 14. With the catheter so positioned, a physician looking through an optical viewing means (not shown) of the endoscope will be able to view an area of the blood vessel adjacent the endoscope's distal end which has been cleared of blood in accordance with the present invention, to be described below. An endoscope which is suitable is described in my co-pending U.S. Ser. No. 018,630, filed Feb. 25, 1987, now U.S. Pat. No. 4,736,733.

Tube 12 also defines another channel, a laser fiber channel 48, which also extends through the tube from the tube's proximal end 16 to and through the tube's distal end 14. Channel 48 is connected at the tube's proximal end to conduit branch 50 of connector 18. Branch 50 and channel 48 are sized and configured to slidably receive a laser fiber 52 having a distal end 54. Channel 48 is also sized and configured to permit the fiber's distal end 54 to be extended outwardly beyond the tube's distal end 14, as such is illustrated in FIGS. 1 and 2. The laser fiber's proximal end is attached to a suitable source of laser energy.

The ability to extend the laser fiber's distal end outwardly beyond the tube's distal end enables a physician viewing the fiber's distal end 54 through catheter 46 of the endoscope to precisely position end 54 near a blood vessel obstruction 56. This enables a physician to remove a blood vessel obstruction by irradiating it with sufficient laser energy transmitted through the fiber.

To view the interior of a blood vessel with catheter system 10 of the present invention, one first inserts a conventional Seldinger type needle (not shown) having a removable obturator (not shown) into the desired blood vessel fairly close to the point of entry in the skin. The obturator is then removed from the needle which allows blood to flow out of the needle. A physician can tell whether the desired artery or vessel has been entered by gaging the color of the blood and its flow rate intensity.

After entering the desired blood vessel, the physician introduces a conventional guide wire (not shown) into the blood vessel through the Seldinger-type needle. The guide wire is preferably fed into the blood vessel in a direction downstream or with the flow of blood through the vessel. However, in some situations, it may be introduced retrograde.

The guide wire is fed until its distal end reaches the area of the blood vessel requiring treatment and/or observation. The Seldinger needle is then removed from the guide wire which enables the physician to insert the catheter tube's distal end 14 into the blood vessel over the guide wire. This is accomplished by feeding the tube via its laser fiber channel 48 over the exposed or proximal end of the guide wire. Feeding of the tube into the blood vessel is continued until the tube's distal end 14 reaches the distal end of the guide wire. The guide wire is then removed from the tube by withdrawing it from channel 48.

Sleeve 24 is then inflated with pressurized fluid such as water or carbon dioxide to stop blood flow through the vessel. This requires that the sleeve be inflated until it expands up against the wall of blood vessel 20. With blood flow stopped, valve 36 controlling the flow of pressurized fluid into the sleeve is preferably shut-off. Carbon dioxide embolyzing gas is then introduced into the blood vessel via channels 38 of the tube at a pressure close to the patient's diastolic pressure. This creates a controlled carbon dioxide embolism on the downstream side of the inflated sleeve as illustrated in FIGS. 1 and 2 which clears blood away from the downstream side of the inflated sleeve. This blood-free area could not be established and maintained if carbon dioxide were not introduced into the blood vessel at the patient's diastolic pressure. Downstream blood from tributaries such as tributaries 58 and 60 would flow backwards, i.e, upstream against the inflated sleeve, and fill the blood-free area occupied by the embolism.

The interface between the downstream blood and carbon dioxide creates and a wall 62 of blood maintained by the $CO_2$ embolism. Wall 62 can be moved downstream or upstream somewhat (that is the size of the embolism can be controlled to an extent) by increasing or decreasing the flow of carbon dioxide into the blood vessel. Increased carbon dioxide flow will move the wall downstream somewhat thereby increasing the size of the embolism. Decreasing the flow of carbon dioxide will accomplish the opposite. However, the flow rate cannot be decreased to the point where pressure drops below the patient's diastolic pressure. If it does, the blood's affinity for carbon dioxide will cause it to quickly absorb the carbon dioxide and thereby quickly back-flow up against the inflated sleeve.

There is also a maximum amount of carbon dioxide which can be introduced into the body. This limit is discussed in U.S. Pat. No. 3,870,072 issuing to Lindemann on Mar 11, 1975 which states that carbon dioxide when absorbed by the blood increases the natural carbonic acid present in venous blood due to muscular work. If under normal conditions more than about 200 mg.'s of carbon dioxide per minute is artificially introduced the dissolving power of the blood may be exceeded and gas bubbles may form in the main coronary vein, endangering the life of the patient.

While this problem of $CO_2$ build-up is certainly serious, it can be alleviated by mechanically ventilating the patient with supplemental air containing between about 25% and 30% oxygen. This increases the rate at which a patient is capable of expiring carbon dioxide from his lungs and thus prevents $CO_2$ build-up in the patient's body.

Returning to FIGS. 1 and 2, it can be seen that tube 12 is preferably inserted into the blood vessel in a downstream direction, as previously described, so that the inflated sleeve will stop the direct or antegrade flow of blood through the vessel. While this downstream orientation of tube 12 is preferred, there may be circumstances where it is necessary to insert the catheter against the flow of blood, i.e., with an upstream orientation. With this orientation, inflated sleeve 24 would not stop the direct or antegrade flow of blood but rather the flow of blood trying to back-fill into the embolism. The direct flow of blood would be stopped by the carbon dioxide embolism. However, to stop such direct flow, the embolism will have to be supplied with carbon dioxide at a higher flow rate than that required to prevent blood back filling, i.e., when tube 12 is oriented in its downstream direction.

Regardless of the catheter's orientation, once a carbon dioxide embolism is established against the inflated sleeve, the area of blood cleared by the embolism may be observed through endoscope 46. If the observed area contains a blood vessel obstruction such as blood vessel obstruction 56, laser fiber 52 may be inserted through channel 48 and positioned so that its distal end 54 is located near the obstruction. The physician will be able to precisely locate the fiber's distal end 54 against blood vessel obstruction 56 since he or she will be able to observe the position of fiber's end through the endoscope. If the physician determines the fiber's end is too far away from the obstruction, the physician can simply move the fiber end closer to the obstruction. The obstruction can then be removed or vaporized by irradiating it with sufficient laser energy which is transmitted through the fiber from a source of laser energy.

From the foregoing description, a number of significant advantages of the present invention should be readily apparent. The ability to establish and maintain a controlled carbon dioxide embolism in a patient's blood vessel provides physicians with the ability to observe the interior of the blood vessel for an extended period of time. This will enable physicians to perform procedures and treatments in the blood vessel which are yet unheard of. Moreover, it will greatly enhance the efficacy of intra-arterial procedures now being performed and/or under development.

This invention has been described in detail with reference to particular embodiments thereof, but it will be understood that various other modifications can be effected within the spirit and scope of this invention.

I claim:

1. A method for forming and maintaining a gas embolism in a portion of a blood vessel of a patient having a site, which is the subject of an operative or investigative procedure, said method including the steps of:
   providing a controlled obstruction to blood flow in a blood vessel;
   introducing gas into the blood vessel at a location adjacent the controlled obstruction continuously at a pressure above the diastolic pressure of the patient to create a controlled embolism in the vessel from the obstruction to a location beyond the site to form a wall of blood beyond the site so that the gas embolism occupies the entire portion of the blood vessel from the obstruction to the wall of blood during the entire duration of the operative procedure; and
   continuously ventilating the patient during the previous steps to minimize elevated gas levels in the patient's bloodstream.

2. A method, as claimed in claim 1, wherein:
   the gas is introduced into the bloodstream on the downstream side of the controlled obstruction.

3. A method, as claimed in claim 1, wherein:
   the pressure and flow rate of the gas being introduced into the blood vessel is varied to control the size of the embolism.

4. A method, as claimed in claim 1, including the further steps of:
   locating and making the embolism of such a size as to include an undesirable blood vessel obstruction; and
   inserting means into the embolism for viewing the obstruction.

5. A method, as claimed in claim 4, including the further steps of:
   inserting means for removing the undesirable blood vessel obstruction into the embolism; and
   removing the undesirable blood vessel obstruction.

6. A method, as claimed in claim 5, including the further steps of:
   removing the removing means from the embolism;
   reducing the gas pressure so that the embolism collapses; and
   removing the controlled obstruction so that normal blood flow can resume.

7. A method for forming and maintaining a gas embolism in a portion of a blood vessel having a site, which is the subject of an operative or investigative procedure, with a catheterization device that includes a flexible tube having a distal end, a proximal end and an outer surface extending between said ends, the tube defining a channel for conducting embolyzing gas from the proximal end through the distal end of the tube to form a controlled gas embolism to clear blood from the portion of a blood vessel and form a wall of blood beyond the site during an operative or investigative procedure, the tube also defining a fluid communicating conduit and port for conducting pressurized fluid from the proximal end through the port which opens onto the outer surface of the tube at a location adjacent the distal end of the tube, the catheterization device also including an inflatable sleeve having opposite ends, the sleeve fitting over the tube and being positioned such that the sleeve covers the port, the sleeve also being sealed to the outer surface of the tube at the opposite ends thereof so that pressurized fluid conducted through the conduit and port is capable of inflating the sleeve to stop blood flow in a blood vessel, said method comprising the steps of:
   inserting the distal end of the catheter into the blood vessel;
   inflating the inflatable sleeve with pressurized fluid conducted through the conduit and port so that the sleeve expands up against the wall of the vessel to create a controlled obstruction to the flow of blood through the vessel;
   introducing gas into the blood vessel at the distal end of the tube via the channel to create a controlled embolism in the blood vessel from the controlled obstruction to a location beyond the site to form a wall of blood beyond the site so that the gas embolism occupies the entire portion of the blood vessel from the obstruction to the wall of blood for the duration of an investigative or operative procedure;
   conducting an investigative or operative procedure within the controlled gas embolism; and
   continuously ventilating the patient during the previous steps to minimize elevated gas levels in the patient's bloodstream.

8. A method, as claimed in claim 7 wherein the conducting step further comprises:
   extending a catheter of an endoscope through said proximal end to the distal end of the tube; and
   viewing the blood free portion of the blood vessel created by the controlled gas embolism by looking through the endoscope.

9. A method, as claimed in claim 8 including the further steps of:
   extending the controlled gas embolism to include an undesirable obstruction in the blood vessel;
   providing the tube with a laser fiber channel which is sized and configured to slidably receive a laser fiber having a distal end;
   inserting the distal end of the laser fiber into the laser fiber channel;
   feeding the laser fiber into the channel so that the fiber's distal end extends outwardly beyond the distal end of the tube into the controlled gas embolism;
   positioning the fiber's outwardly extending distal end near the undesirable blood vessel obstruction within the controlled gas embolism so that laser energy transmitted by said fiber is capable of irradiating and removing the undesirable blood vessel obstruction; and
   transmitting sufficient laser energy through the laser fiber to irradiate and remove the undesirable blood vessel obstruction.

10. A method, as claimed in claim 9, including the further steps of:
    viewing the distal end of the laser fiber through the endoscope within the controlled gas embolism to facilitate said positioning of the fiber near the undesirable blood vessel obstruction.

* * * * *